United States Patent
Cornwall et al.

(10) Patent No.: US 8,652,177 B1
(45) Date of Patent: Feb. 18, 2014

(54) SYSTEMS AND METHODS FOR TREATING SPINAL DEFORMITIES

(75) Inventors: G. Bryan Cornwall, San Diego, CA (US); Jonathan Spangler, Del Mar, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 13/438,828

(22) Filed: Apr. 3, 2012

Related U.S. Application Data

(63) Continuation of application No. 11/490,995, filed on Jul. 20, 2006, now Pat. No. 8,147,521.

(60) Provisional application No. 60/701,308, filed on Jul. 20, 2005.

(51) Int. Cl.
*A61B 17/70* (2006.01)

(52) U.S. Cl.
USPC .......... 606/265; 606/266; 623/17.16

(58) Field of Classification Search
USPC ............... 606/246–279; 623/17.16
See application file for complete search history.

(56) References Cited

U.S. PATENT DOCUMENTS

| | | | |
|---|---|---|---|
| 3,426,364 A | 2/1969 | Lumb | |
| 4,667,664 A | 5/1987 | Taylor et al. | |
| 4,743,256 A | 5/1988 | Brantigan | |
| 4,834,757 A | 5/1989 | Brantigan | |
| 4,877,020 A | 10/1989 | Vich | |
| 4,878,915 A | 11/1989 | Brantigan | |
| 4,950,296 A | 8/1990 | McIntyre | |
| 4,961,740 A | 10/1990 | Ray et al. | |
| 5,026,373 A | 6/1991 | Ray et al. | |
| 5,055,104 A | 10/1991 | Ray | |
| 5,171,278 A | 12/1992 | Pisharodi | |
| 5,192,327 A * | 3/1993 | Brantigan | 623/17.11 |
| 5,254,118 A | 10/1993 | Mirkovic | |
| 5,304,210 A | 4/1994 | Crook | |
| 5,306,307 A | 4/1994 | Senter et al. | |
| 5,306,309 A | 4/1994 | Wagner et al. | |
| 5,334,204 A * | 8/1994 | Clewett et al. | 606/312 |
| 5,397,364 A | 3/1995 | Kozak et al. | |
| 5,425,772 A | 6/1995 | Brantigan | |
| 5,443,514 A | 8/1995 | Steffee | |
| 5,458,638 A | 10/1995 | Kuslich et al. | |
| 5,484,437 A | 1/1996 | Michelson | |
| 5,489,308 A | 2/1996 | Kuslich et al. | |
| 5,514,180 A | 5/1996 | Heggeness et al. | |
| 5,522,899 A | 6/1996 | Michelson | |
| 5,593,409 A | 1/1997 | Michelson | |
| 5,607,424 A | 3/1997 | Tropiano | |
| 5,609,636 A | 3/1997 | Kohrs et al. | |
| 5,645,598 A | 7/1997 | Brosnahan et al. | |

(Continued)

FOREIGN PATENT DOCUMENTS

| | | |
|---|---|---|
| CA | 2015507 | 1/1999 |
| EP | 369603 | 5/1990 |

(Continued)

*Primary Examiner* — Jerry Cumberledge
(74) *Attorney, Agent, or Firm* — Jonathan Spangler; Rory Schermerhorn

(57) ABSTRACT

Systems and methods of treating spinal deformity, including one or more intervertebral implants to be introduced laterally into respective intervertebral spaces, a plurality of bone screws introduced generally laterally into vertebral bodies adjacent to the intervertebral implants and/or the intervertebral implants themselves, and a cable dimensioned to be coupled to the bone screws and manipulated to adjust and/or correct the spinal deformity.

23 Claims, 8 Drawing Sheets

(56) References Cited

U.S. PATENT DOCUMENTS

| | | |
|---|---|---|
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs et al. |
| 5,662,710 A | 9/1997 | Bonutti |
| 5,665,122 A | 9/1997 | Kambin |
| 5,669,909 A | 9/1997 | Zdeblick et al. |
| 5,683,391 A | 11/1997 | Boyd |
| 5,683,394 A | 11/1997 | Rinner |
| 5,683,464 A | 11/1997 | Wagner et al. |
| 5,700,291 A | 12/1997 | Kuslich et al. |
| 5,702,449 A | 12/1997 | McKay |
| 5,716,415 A | 2/1998 | Steffee |
| 5,720,748 A | 2/1998 | Kuslich et al. |
| 5,728,159 A | 3/1998 | Stroever et al. |
| 5,741,253 A | 4/1998 | Michelson |
| 5,766,252 A * | 6/1998 | Henry et al. ............... 623/17.16 |
| 5,772,661 A | 6/1998 | Michelson |
| 5,782,830 A | 7/1998 | Farris |
| 5,782,919 A | 7/1998 | Zdeblick et al. |
| 5,785,710 A | 7/1998 | Michelson |
| 5,797,917 A | 8/1998 | Boyd et al. |
| 5,814,084 A | 9/1998 | Grivas et al. |
| 5,860,973 A | 1/1999 | Michelson |
| 5,865,845 A | 2/1999 | Thalgott |
| 5,865,846 A | 2/1999 | Bryan et al. |
| 5,865,848 A | 2/1999 | Baker |
| 5,885,299 A | 3/1999 | Winslow et al. |
| 5,888,224 A | 3/1999 | Beckers et al. |
| 5,893,890 A | 4/1999 | Pisharodi |
| 5,904,719 A | 5/1999 | Errico et al. |
| 5,968,098 A | 10/1999 | Winslow |
| 6,004,326 A | 12/1999 | Castro et al. |
| 6,033,405 A | 3/2000 | Winslow et al. |
| 6,045,580 A | 4/2000 | Scarborough et al. |
| 6,059,829 A | 5/2000 | Schlapfer et al. |
| 6,063,088 A | 5/2000 | Winslow |
| 6,066,175 A | 5/2000 | Henderson et al. |
| 6,080,158 A * | 6/2000 | Lin ............... 606/247 |
| 6,083,225 A | 7/2000 | Winslow et al. |
| 6,096,080 A | 8/2000 | Nicholson et al. |
| 6,102,948 A | 8/2000 | Brosnahan, III |
| 6,106,557 A | 8/2000 | Robioneck et al. |
| 6,120,503 A | 9/2000 | Michelson |
| 6,120,506 A | 9/2000 | Kohrs et al. |
| 6,143,033 A | 11/2000 | Paul et al. |
| 6,156,037 A | 12/2000 | LeHuec et al. |
| 6,159,211 A * | 12/2000 | Boriani et al. ............... 606/279 |
| 6,159,245 A | 12/2000 | Meriwether et al. |
| 6,176,882 B1 | 1/2001 | Biedermann et al. |
| 6,200,347 B1 | 3/2001 | Anderson et al. |
| 6,206,922 B1 | 3/2001 | Zdeblick et al. |
| 6,224,607 B1 | 5/2001 | Michelson |
| 6,224,631 B1 | 5/2001 | Kohrs |
| 6,241,771 B1 | 6/2001 | Gresser et al. |
| 6,251,140 B1 | 6/2001 | Marino et al. |
| 6,258,125 B1 | 7/2001 | Paul et al. |
| 6,277,149 B1 | 8/2001 | Boyle et al. |
| 6,296,647 B1 | 10/2001 | Robioneck et al. |
| 6,306,170 B2 | 10/2001 | Ray |
| RE37,479 E | 12/2001 | Kuslich |
| 6,325,827 B1 * | 12/2001 | Lin ............... 623/17.16 |
| 6,371,989 B1 | 4/2002 | Chauvin et al. |
| 6,383,221 B1 | 5/2002 | Scarborough et al. |
| 6,409,766 B1 | 6/2002 | Brett |
| 6,432,140 B1 * | 8/2002 | Lin ............... 623/17.16 |
| 6,447,547 B1 | 9/2002 | Michelson |
| 6,468,311 B2 | 10/2002 | Boyd et al. |
| 6,491,724 B1 | 12/2002 | Ferree |
| 6,527,773 B1 | 3/2003 | Lin et al. |
| D472,634 S | 4/2003 | Anderson |
| D473,650 S | 4/2003 | Anderson |
| 6,547,823 B2 | 4/2003 | Scarborough et al. |
| 6,635,086 B2 | 10/2003 | Lin |
| 6,648,895 B2 | 11/2003 | Burkus et al. |
| 6,676,703 B2 | 1/2004 | Biscup |
| 6,695,845 B2 | 2/2004 | Dixon et al. |
| 6,695,851 B2 | 2/2004 | Zdeblick et al. |
| 6,702,823 B2 | 3/2004 | Iaia |
| 6,743,255 B2 | 6/2004 | Ferree |
| 6,746,484 B1 | 6/2004 | Liu et al. |
| 6,824,564 B2 | 11/2004 | Crozet |
| D503,801 S | 4/2005 | Jackson |
| 6,899,714 B2 | 5/2005 | Vaughan |
| 6,942,698 B1 | 9/2005 | Jackson |
| 6,964,687 B1 | 11/2005 | Bernard et al. |
| 6,979,353 B2 | 12/2005 | Bresina |
| 6,984,245 B2 | 1/2006 | McGahan et al. |
| 6,986,788 B2 | 1/2006 | Paul et al. |
| 6,989,031 B2 | 1/2006 | Michelson |
| 7,018,416 B2 | 3/2006 | Hanson et al. |
| D530,423 S | 10/2006 | Miles et al. |
| 2001/0025180 A1 | 9/2001 | Jackson |
| 2002/0055738 A1 | 5/2002 | Lieberman |
| 2002/0107572 A1 | 8/2002 | Foley et al. |
| 2002/0116065 A1 | 8/2002 | Jackson |
| 2002/0138146 A1 | 9/2002 | Jackson |
| 2003/0088251 A1 | 5/2003 | Braun et al. |
| 2003/0105528 A1 | 6/2003 | Shimp et al. |
| 2003/0109928 A1 | 6/2003 | Pasquet et al. |
| 2003/0125739 A1 | 7/2003 | Bagga et al. |
| 2003/0139812 A1 | 7/2003 | Garcia et al. |
| 2004/0034353 A1 | 2/2004 | Michelson |
| 2004/0122424 A1 | 6/2004 | Ferree |
| 2004/0249379 A1 | 12/2004 | Winslow |
| 2005/0033432 A1 | 2/2005 | Gordon et al. |
| 2005/0071008 A1 | 3/2005 | Kirschman |
| 2005/0101960 A1 | 5/2005 | Fiere |
| 2005/0159813 A1 | 7/2005 | Molz |
| 2005/0203538 A1 | 9/2005 | Lo et al. |
| 2005/0228501 A1 | 10/2005 | Miller et al. |
| 2005/0256578 A1 | 11/2005 | Blatt et al. |
| 2006/0036243 A1 | 2/2006 | Sasso |
| 2006/0074490 A1 | 4/2006 | Sweeney |
| 2006/0217807 A1 * | 9/2006 | Peterman et al. .......... 623/17.11 |

FOREIGN PATENT DOCUMENTS

| | | |
|---|---|---|
| EP | 716840 | 6/1996 |
| EP | 784967 | 7/1997 |
| EP | 796593 | 9/1997 |
| EP | 880938 | 2/1998 |
| EP | 1188424 | 3/2002 |
| GB | 2294399 | 5/1996 |
| WO | WO-91/06261 | 5/1991 |
| WO | WO-96/08205 | 3/1996 |
| WO | WO-97/33525 | 9/1997 |
| WO | WO-97/37620 | 10/1997 |
| WO | WO-98/09586 | 3/1998 |
| WO | WO-98/17208 | 4/1998 |
| WO | WO-99/08627 | 2/1999 |
| WO | WO-99/38461 | 8/1999 |

* cited by examiner

SYSTEMS AND METHODS FOR TREATING SPINAL DEFORMITIES

CROSS-REFERENCES TO RELATED APPLICATIONS

This application is a continuation of U.S. patent application Ser. No. 11/490,995, (Now U.S. Pat. No. 8,147,521), filed Jul. 20, 2006, which claims the benefit of priority from U.S. Provisional Patent Application Ser. No. 60/701,308, filed on Jul. 20, 2005, the entire contents of which are each expressly incorporated by reference into this disclosure as if set forth fully herein.

BACKGROUND OF THE INVENTION

I. Field of the Invention

The present invention relates generally to surgical fixation and, more particularly, to systems and methods for treating spinal deformities.

II. Discussion of the Prior Art

The human spine exhibits some degree of curvature at different levels to facilitate normal physiologic function. Correction of the spine may be required when the curvature of the spine deviates substantially from normal. The misalignment usually manifests itself in an asymmetry of the vertebral bodies, such that, over a sequence of vertebrae, the spine twists and/or bends to one side. This lateral deviation of the spine is commonly termed scoliosis.

Spinal deformity occurs when a patient has abnormal frontal or sagittal plane alignment. At the same time, the cervical and lumbar spine exhibit lordosis, while the thoracic spine has kyphosis. Thus, when performing spinal fusion, surgeons may be required to preserve or restore both front plane and sagittal alignment while taking lordosis and kyphosis into account. Scoliosis can develop later in life, as joints in the spine degenerate and create a bend in the back which may require surgery.

Surgery has traditionally involved procedures such as the Harrington, Dwyer and Zielke, and Luque procedures which rely on implanted rods, laminar/pedicle hooks, and screws to maintain the correction until stabilized by fusion of vertebrae. According to these surgical techniques, treating scoliosis includes the implantation of a plurality of hooks and/or screws into the spinal bones, connecting rods to these elements, physically bracing the bones into the desired positions, and permitting the bones to fuse across the entire assembly. This immobilization often requires anterior plates, rods and screws and posterior rods, hooks and/or screws. Alternatively, spacer elements are positioned between the sequential bones, which spacers are often designed to permit fusion of the bone into the matrix of the spacer from either end, hastening the necessary rigidity of the developing bone structure.

The Harrington instrumentation system has been used successfully for some time, but because the distraction rod is fixed to the spine in only two places, failure at either end causes the entire system to fail. Another deficiency with existing mechanisms and approaches is that the single rod used to correct the defects must be contoured to fit various attachment sites. In patients having compound spinal deformity, this may be extremely difficult. A further problem is that the contoured rod frequently limits further correction of certain types of deformities. That is, once the rod is in position, further correction of the deformity is difficult, since existing systems tend to limit incremental alignment procedures.

The present invention is directed at overcoming, or at least improving upon, the disadvantages of the prior art.

SUMMARY OF THE INVENTION

The present invention accomplishes this goal by providing a spinal alignment system that may be affixed to a plurality of vertebra via any number of suitable techniques, such as open surgery or minimally invasive surgery. The spinal alignment system can take the form of either a single level system or a multi-level system. Fixing adjacent vertebra in this manner is advantageous in that it provides a desired level of flexibility to parts of the spine, while also providing long-term durability and consistent stabilization.

According to one broad aspect of the present invention, a single level spinal alignment system includes a cable, a superior bone screw, an inferior bone screw, and at least one spinal fusion implant. This single level spinal alignment system may be used to treat spinal deformities, including but not limited to scoliosis. To do so, access may be provided through a lateral approach utilizing either an open or a minimally invasive technique. According to one aspect of the present invention, a spinal fusion implant is introduced into a targeted intervertebral space after access has been achieved. A superior bone screw and an inferior bone screw may thereafter be anchored into the immediately superior and immediately inferior vertebral bodies, respectively, on either side of the targeted intervertebral space. According to one embodiment, the cable may be locked to the superior bone screw and thereafter pulled or otherwise manipulated such that the distance between the superior bone screw and inferior bone screw is reduced. This serves to move the superior and inferior vertebral bodies so as to correct or minimize the spinal deformity. After this reduction, the cable may be locked to the inferior bone screw to maintain the superior and inferior vertebral bodies in the resulting configuration. In addition to manner described above, it is also contemplated that the cable may be coupled to the superior bone screw prior to introducing the inferior bone screw.

According to one broad aspect of the present invention, a multi level spinal alignment system comprises a cable, a superior bone screw, an inferior bone screw, at least one middle bone screw, and at least one spinal fusion implant. The multi level spinal alignment system of the present invention may be used to treat spinal deformities, including but not limited to scoliosis. To do so, access may be provided through a lateral approach utilizing either an open or minimally invasive technique. According to one aspect of the present invention, a plurality of spinal fusion implants are introduced into targeted intervertebral spaces after access has been achieved. A superior bone screw is introduced into the vertebral body immediately superior to the highest of the spinal fusion implants. An inferior bone screw is introduced into the vertebral body immediately inferior to the lowest of the spinal fusion implants. A middle bone screw is introduced into each vertebral body in between the superior bone screw and the inferior bone screw.

According to one embodiment, the cable may be threaded or otherwise passed through apertures in the middle screws, and thereafter locked to the superior bone screw. The cable may then be pulled or otherwise manipulated such that the distance between the superior bone screw, the inferior bone screw, and any middle bone screws is reduced. This serves to move the superior vertebral body, the inferior vertebral body, and any intermediate vertebral bodies so as to correct or minimize the spinal deformity. After this reduction, the cable may be locked to the middle bone screws and inferior bone screw to maintain the superior vertebral body, inferior vertebral body, and any intermediate vertebral bodies in the resulting configuration. In addition to manner described above, it is also contemplated that the cable may be coupled to one of the bone screws (e.g. the superior bone screw) prior to introducing the other bone screws (e.g. the inferior bone screw).

The cable is an elongated flexible member with a first end, a second end, a head member located at the first end, and a main portion extending from the head member to the second end. The head member of the cable is preferably located at one end of the cable. The head member may be a spherical body shaped to be relieved within and locked into the superior bone screw. The head member may also be dimensioned in any number of suitable shapes necessary to facilitate surgical fixation, including but not limited to oval, flat or rectangular. The head member may also include an aperture extending generally perpendicularly through the surface of the head member to accept a post or other purchase element provided on the superior bone screw.

The main portion may be composed of any substantially and suitable flexible material capable of performing spinal alignment including, but not limited to, steel, nylon, plastics, or various composites. Accordingly, any suitable shape for the cable is useable, whether cylindrical, flat, square, or other suitable shapes and configurations within the scope of the present invention. The main portion of the cable may also include a plurality of apertures located near the proximal or second end of the cable whereby the apertures extend generally perpendicularly through the surface of the cable. As is described in detail below, the cable is used to straighten curvature in the spine.

The superior bone screw may either be fixed-angle or polyaxial. Fixed-angle screws and polyaxial screws are generally known in the art and will not be further explained herein. Other fasteners or anchors may also be used, such as those commonly used in surgical fixation procedures. The superior bone screw may be cannulated in order to allow precise insertion with the use of a K-wire or other surgical insertion-facilitating device that may be commonly used in such a procedure. The superior bone screw may include a receiving post instead of the usual receiving head on a fixed and polyaxial screw.

The inferior bone screw may either be fixed-angle or polyaxial. Other fasteners or anchors may be used, such that is commonly used in surgical fixation procedures. The inferior bone screw may be cannulated in order to allow precise insertion with the use of a K-wire or other surgical insertion-facilitating device that may be commonly used in such a procedure. The inferior bone screw may include a receiving post instead of the usual receiving head on a fixed and polyaxial screw.

The middle bone screw(s) may be either fixed-angle or polyaxial. It should also be noted that the middle bone screw(s) may include an aperture located on the head of the screw. Each aperture has a substantially spherical inside surface with a top diameter and a bottom diameter with a circular shape. It should be noted that any combination of fixed and/or polyaxial screws may be used in connection with the superior bone screw, the inferior bone screw, and/or the middle bone screw(s).

The spinal fusion implants are of non-bone construction and may be provided in any number of suitable shapes and sizes depending upon the particular surgical need. The spinal fusion implant may be dimensioned for use in the cervical and/or lumbar spine in any variety of ways, such as the design described in commonly owned and co-pending U.S. patent application Ser. No. 11/093,409, the entire contents of which are hereby expressly incorporated by reference into this disclosure as if set forth fully herein.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal alignment system disclosed herein boasts a variety of inventive features and components that warrant patent protection, both individually and in combination.

Figure 1:
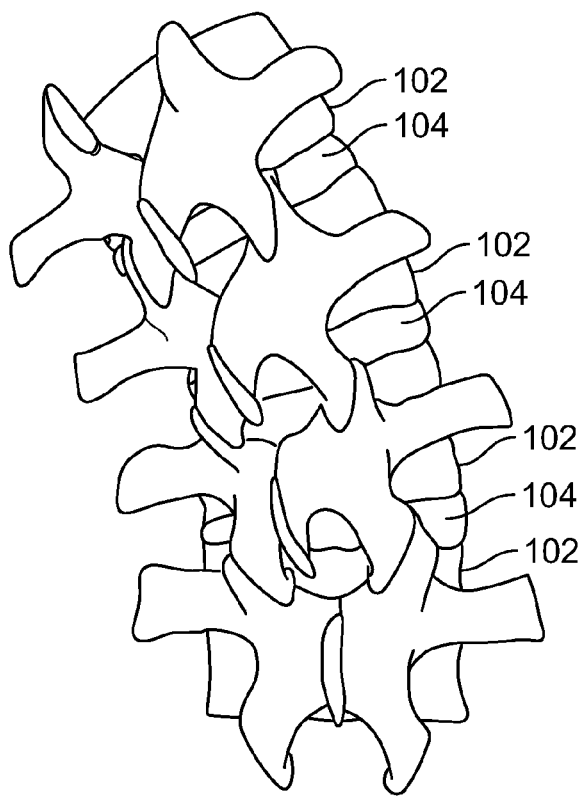
FIG. 1 is a front view of a human spine having scoliosis.

FIG. 1 shows a human spine (comprising vertebrae 102 and intervertebral discs 104) with scoliosis, which is in need of correction according to the present invention. As will be described in detail below, the present invention accomplishes this by providing a spinal alignment system comprising one or more spinal fusion implants, a plurality of bone screws, and a cable which cooperate to correct or minimize the particular spinal deformity. The spinal alignment system can take the form of either a single level system or a multi-level system. Fixing adjacent vertebra in this manner is advantageous in that it provides a desired level of flexibility to parts of the spine, while also providing long-term durability and consistent stabilization.

Figure 2:
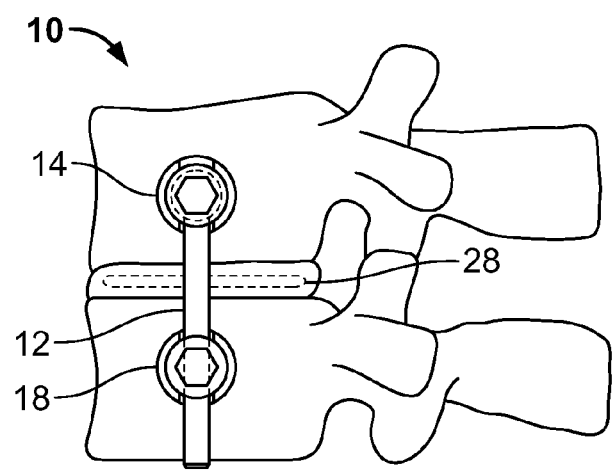
FIG. 2 is a lateral view of a single level spinal alignment system according to a first embodiment of the present invention.
Figure 3:
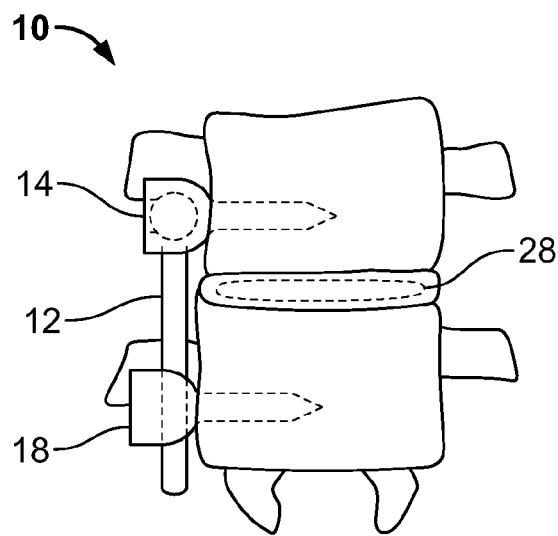
FIG. 3 is an anterior view of the single level spinal alignment system according to the embodiment drawn in FIG. 2.

FIGS. 2-3 are lateral and anterior views (respectively) of a single level spinal alignment system 10 according to a first broad aspect of the present invention. The spinal alignment system 10 includes a cable 12, a superior bone screw 14, an inferior bone screw 18, and at least one spinal fusion implant 28, all of which may be preferably introduced into the patient in a generally lateral direction (via open or minimally invasive techniques). According to one aspect of the present invention, a spinal fusion implant 28 is introduced into a targeted intervertebral space after access has been achieved. A superior bone screw 14 and an inferior bone screw 18 may thereafter be anchored into the immediately superior and immediately inferior vertebral bodies, respectively, on either side of the targeted intervertebral space. As will be appreciated, one or more of the bone screws 14, 18 may be implanted prior to the implant 28 without departing from the scope of the present invention. According to one embodiment, the cable 12 may be locked to the superior bone screw 14 and thereafter pulled or otherwise manipulated such that the distance between the superior bone screw 14 and inferior bone screw 18 is reduced. This serves to move the superior and inferior vertebral bodies so as to correct or minimize the spinal deformity. After this reduction, the cable 12 may be locked to the inferior bone screw 18 to maintain the superior and inferior vertebral bodies in the resulting configuration. In addition to manner described above, it is also contemplated that the cable 12 may be coupled to the superior bone screw 14 prior to introducing the inferior bone screw 18, and that the cable 12 may be coupled to the inferior bone screw 18 before the superior bone screw 14.

Figure 4:
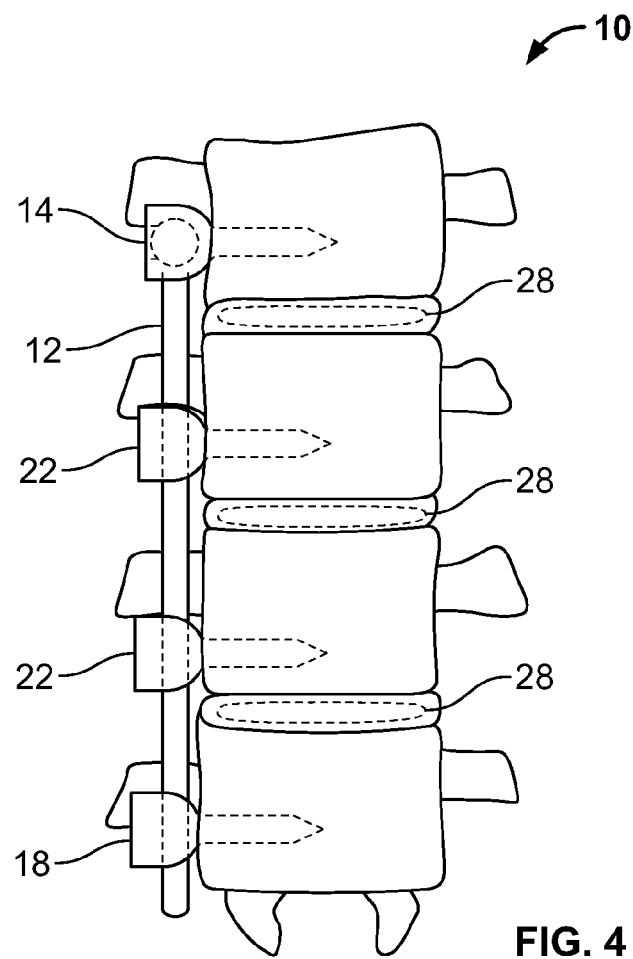
FIG. 4 is an anterior view of a multi-level spinal alignment system according to another embodiment of the present invention.
Figure 5:
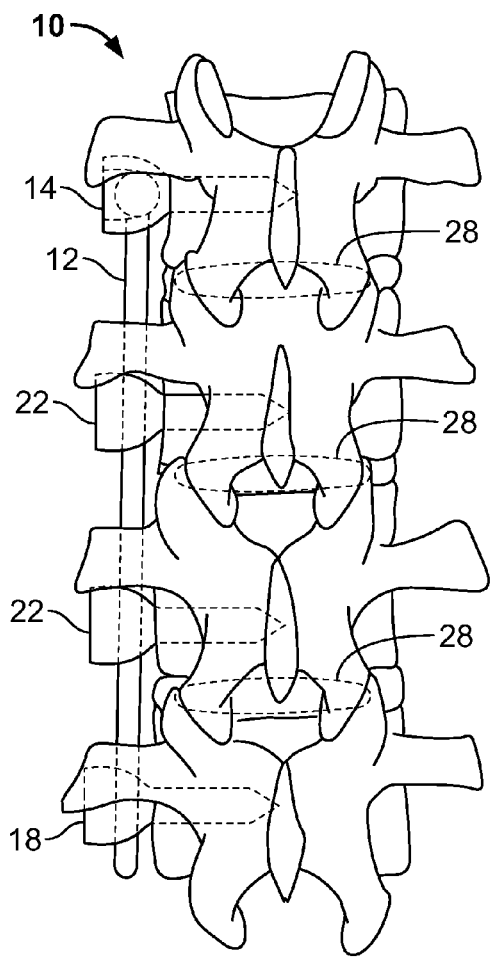
FIG. 5 is a posterior view of the multi-level spinal alignment system according to the embodiment drawn in FIG. 4.
Figure 6:
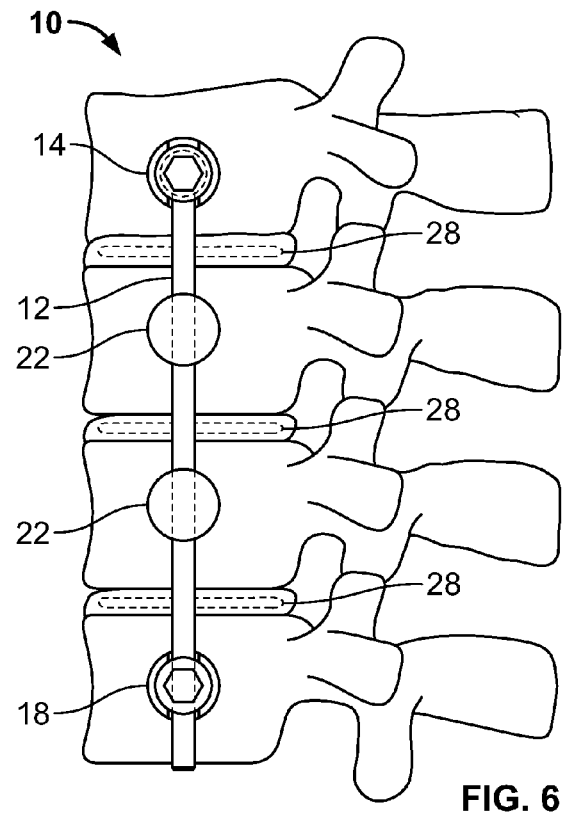
FIG. 6 is a lateral view of the multi level spinal alignment system according to the embodiment drawn in FIG. 4.

FIGS. 4-6 are anterior, posterior, and lateral views (respectively) of a multi-level spinal alignment system 10 according to another broad aspect of the present invention. In addition to the components of the single level embodiment of FIGS. 2-3 (which need not be repeated) the multi level spinal alignment system 10 includes at least one middle bone screw 22 and at least two spinal fusion implants 28, which may also preferably be introduced into the patient in a generally lateral manner (via open or minimally invasive techniques). As will be described with greater detail below, the multi-level spinal alignment system 10 of the present invention may be used to treat spinal deformities, including but not limited to scoliosis. According to one aspect of the present invention, a plurality of spinal fusion implants 28 are introduced into targeted intervertebral spaces after access has been achieved. A superior bone screw 14 is introduced into the vertebral body immediately superior to the highest of the spinal fusion implants 28. An inferior bone screw 18 is introduced into the vertebral body immediately inferior to the lowest of the spinal fusion implants 28. A middle bone screw 22 is introduced into each vertebral body in between the superior bone screw 14 and the inferior bone screw 18. As will be appreciated, the screws 14, 18, 22 and implants 28 may be introduced in any order without departing from the scope of the invention.

According to one embodiment, the cable 12 may be threaded or otherwise passed through apertures in the middle screws 22, and thereafter locked to the superior bone screw. The cable may then be pulled or otherwise manipulated such that the distance between the superior bone screw 14, the inferior bone screw 18, and any middle bone screws 22 is reduced. This serves to move the superior vertebral body, the inferior vertebral body, and any intermediate vertebral bodies so as to correct or minimize the spinal deformity. After this reduction, the cable 12 may be locked to the middle bone screws 22 and inferior bone screw 18 to maintain the superior vertebral body, inferior vertebral body, and any intermediate vertebral bodies in the resulting configuration. In addition to manner described above, it is also contemplated that the cable 12 may be coupled to the superior bone screw 14 prior to introducing the middle bone screws 22 and/or the inferior bone screw 18.

Whether in the single level or multi level embodiments, the bone screws, cable, and fusion implants of the present invention may be provided in any number of suitable manners without departing from the scope of the present invention. For example, with reference to FIG. 7, the bone screws 14, 18, 22 may each be provided having a "tulip style" cable housing 50 coupled to a shaft 52. The cable housing 50 may be integrally formed with the shaft 52 (forming a so-called "fixed axis" screw) or adjustably coupled to the shaft 52 (forming a so-called "poly-axial" screw). Any number of suitable closure mechanisms may be employed to secure the cable 12 to the respective screws 14, 18, 22, including but not limited to the threaded set screws 54. The set screws 54 include an external thread 56 dimensioned to engage within a threaded region 60 provided within each cable housing 50. The shaft 52 includes an externally disposed thread 62, which may be provided having any number of suitable pitches, lengths, widths, etc., depending upon the surgical application and patient anatomy. Other fasteners or anchors may also be used, such as those commonly used in surgical fixation procedures. The bone screws 14, 18, 22 may be cannulated in order to allow precise insertion with the use of a K-wire or other surgical insertion-facilitating device that may be commonly used in such a procedure.

The cable 12 is an elongated flexible member with a first end, a second end, and a head member 30 located at the first end, and a main portion 32 extending from the head member 30 to the second end. The head member 30 of the cable 12 may be a spherical body shaped to be received within and locked into the cable housing 50 of the superior bone screw 14. It should also be noted that the head member 30 may also be dimensioned in any number of suitable shapes necessary to facilitate surgical fixation, including but not limited to spherical, oval, flat, or rectangular depending upon the configuration of the cable housing 50. The main portion 32 may be composed of any substantially and suitable flexible material capable of performing spinal alignment including, but not limited to, steel, nylon, plastics, or various composites. Accordingly, any suitable shape for the cable 12 is useable, whether cylindrical, flat, square, or other suitable shapes and configurations within the scope of the present invention. As is described in detail below, the cable 12 is used to straighten curvature in the spine. It is also within the scope of the present invention that the cable 12 may be substituted for a rigid rod with or without a spherical head.

Figures 7, 8:
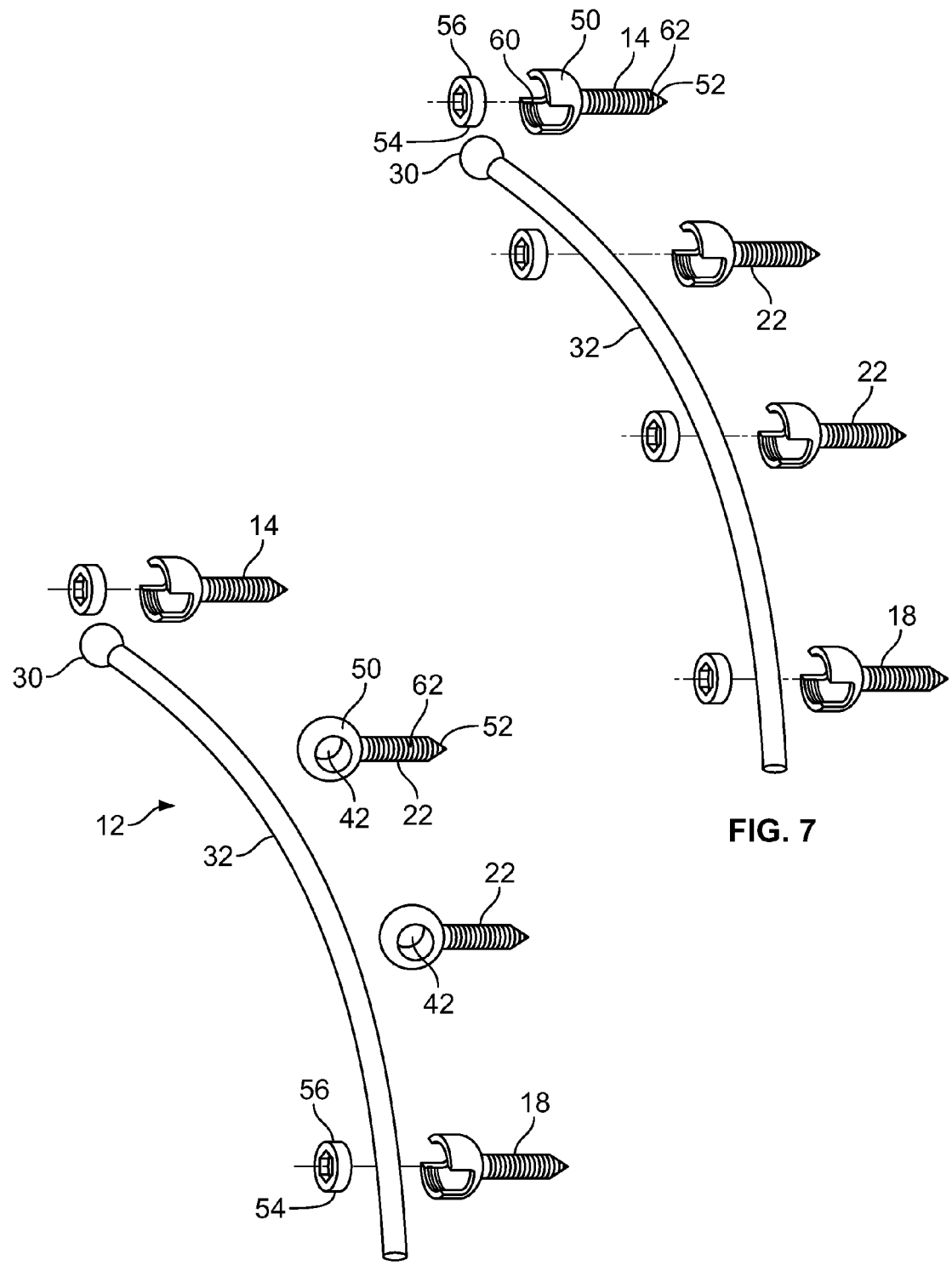
FIG. 7 is a perspective view of a multi-level spinal alignment system according to one embodiment of the present invention.
FIG. 8 is a perspective view of a multi-level spinal alignment system according to another embodiment of the present invention.

FIG. 8 illustrates a still further embodiment of the spinal alignment system 10 of the present invention, wherein the middle screws 22 include a "side-loading" cable housing 50 coupled to the shaft 52. As with the embodiment of FIG. 7, the cable housing 50 may be either integrally formed with the shaft 52 (forming a so-called "fixed axis" screw) or adjustably coupled to the shaft 52 (forming a so-called "poly-axial" screw). In either event, the cable housing 50 of each middle screw 22 includes an aperture 42 extending generally perpendicularly therethrough and dimensioned to receive the main portion 32 of the cable 12. While shown as generally circular in cross section, the aperture 42 may be provided having any number of suitable cross sectional shapes, such as an oval and/or rectangular, depending upon the cross sectional shape of the main section 32 of the cable 12.

In use, the main portion 32 of the cable 12 may be fed or otherwise directed through each aperture 42 (either before or after the head 30 of the cable 12 is locked to the superior bone screw 14). As will be discussed in greater detail below, the aperture 42 of each cable housing 50 is dimensioned such that the main portion 32 will be allowed to traverse therethrough as the spinal alignment system 10 of the present invention is tightened or adjusted to effectuate spinal deformity correction. Once such a correction has been accomplished, the set screw 54 of the inferior screw 18 may be employed to lock the spinal alignment system 10 and thereby maintain the correction.

Figure 9:
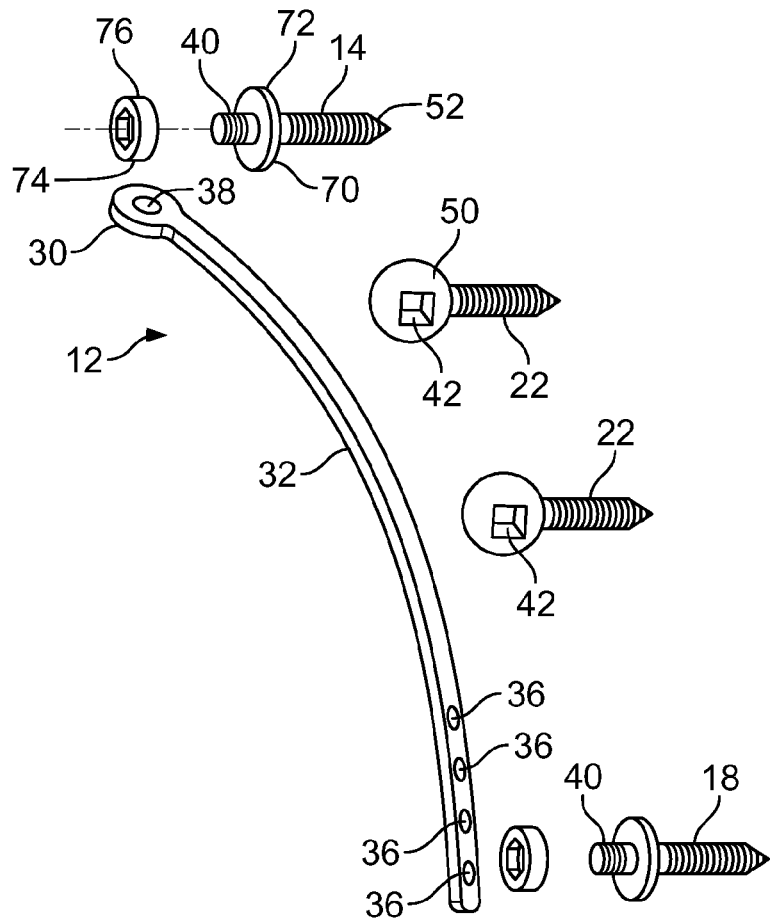
FIG. 9 is a perspective view of a multi level spinal alignment system according to yet another embodiment of the present invention.

FIG. 9 illustrates yet another embodiment of the spinal alignment system 10 of the present invention, wherein the superior and inferior bone screws 14, 18 each have a top-loading "post style" head region 70 (including a threaded post 40 and a ring member 72) coupled to the shaft 52. As with the embodiment of FIGS. 7 and 8, the head region 70 may be either integrally formed with the shaft 52 (forming a so-called "fixed axis" screw) or adjustably coupled to the shaft 52 (forming a so-called "poly-axial" screw). In either event, the threaded post 40 of the superior bone screw 14 is dimensioned to be coupled to a corresponding aperture 38 formed in the head 30 of the cable 12 shown in FIG. 9 (which represents an alternate embodiment relative to that shown in FIGS. 2-8 and which will be described in greater detail below). The threaded post 40 of the inferior bone screw 18 is dimensioned to be coupled to one of several corresponding apertures 36 formed in the main portion 32 according to the alternate embodiment of the cable 12 shown in FIG. 9. The cable housing 50 of each middle screw 22 includes an aperture 42 dimensioned to pass the main portion 32 of the cable 12 therethrough in generally the same manner as the embodiment shown in FIG. 8. Any number of suitable closure mechanisms may be employed to secure the cable 12 to the respective threaded post 40, including but not limited to the threaded nuts 74. The threaded nuts 74 include an internal thread 76 dimensioned to engage with a threaded region provided on each threaded post 40.

Figure 10:
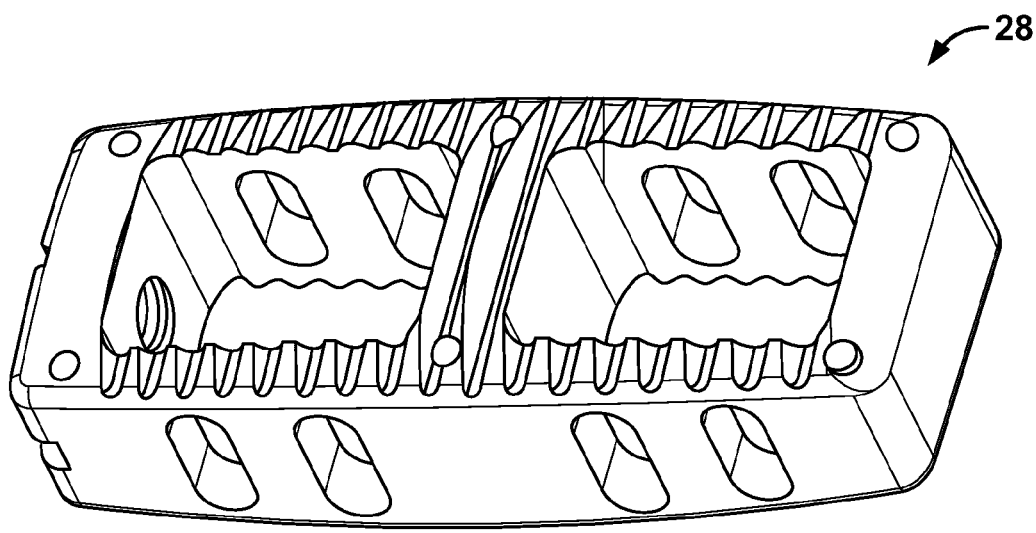
FIG. 10 is a perspective view of a spinal fusion implant according to one embodiment of the present invention.

FIG. 10 illustrates the spinal fusion implants 28 according to one embodiment of the present invention. The non-bone construction of the spinal fusion implant 28 may be provided in any number of suitable shapes and sizes depending upon the particular surgical need. The spinal fusion implant 28 may be dimensioned for use in the cervical and/or lumbar spine in any variety of ways, such as the design described in commonly owned and co-pending U.S. patent application Ser. No. 11/093,409, the entire contents of which are hereby expressly incorporated by reference into this disclosure as if set forth fully herein.

Figure 11:
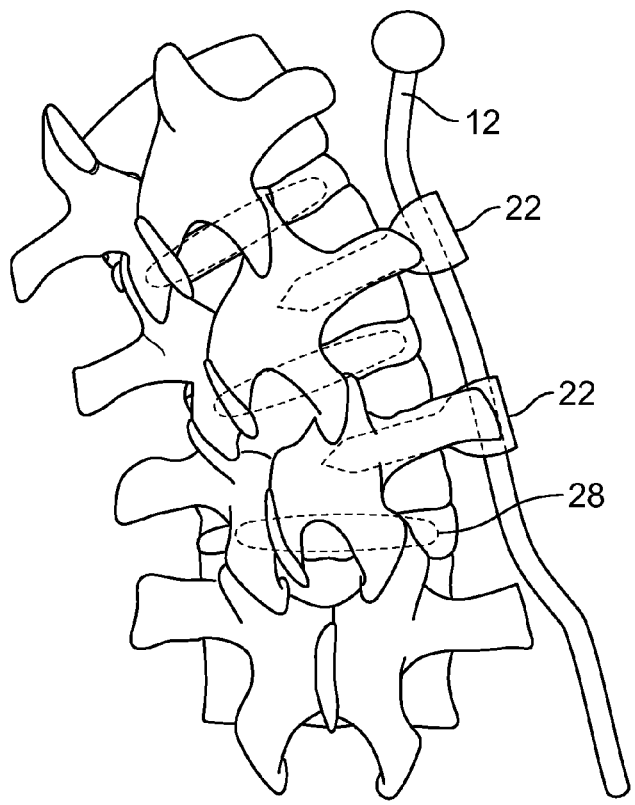
FIG. 11 illustrates aspects of performing multi-level spinal deformity correction according to one embodiment of the present invention.
Figure 12:
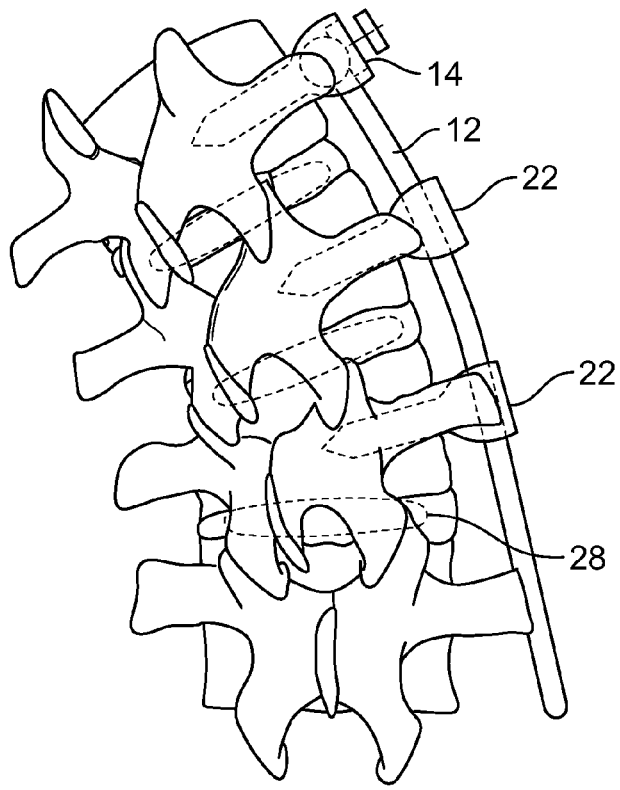
FIG. 12 illustrates aspects of performing multi-level spinal deformity correction according to another embodiment of the present invention.
Figure 13:
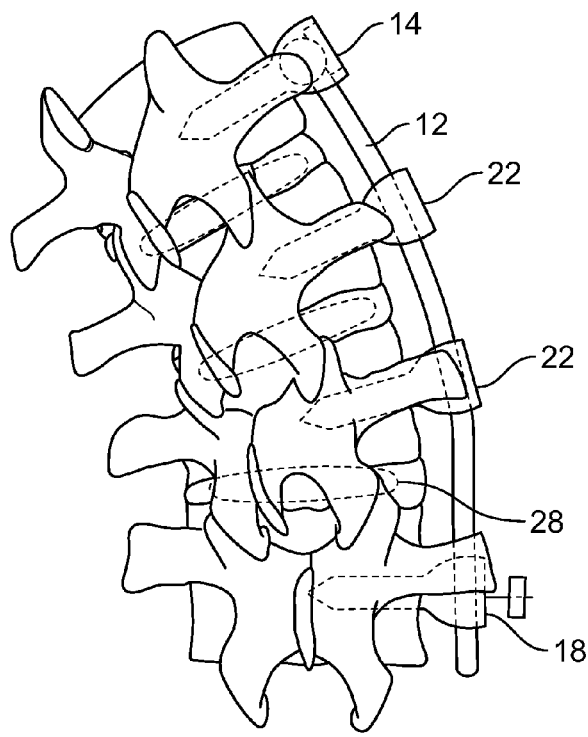
FIG. 13 illustrates aspects of performing multi-level spinal deformity correction according to yet another embodiment of the present invention.

The spinal alignment system 10 of the present invention may be employed using any number of suitable methods in addition to those previously described. FIGS. 11-13 illustrate, by way of example only, one such method of installation of the multi level spinal alignment system 10 of the present invention. In order to use the spinal alignment system 10 of the present invention in a treatment of degenerative scoliosis, a clinician must first designate the appropriate spinal fusion implant size 28. A clinician can utilize the spinal alignment system 10 in either an open or minimally invasive technique involving a generally lateral approach. In either type of procedure, a working channel must be created in a patient that reaches a targeted spinal level. According to the present invention, the preferred approach for creating this working channel is from the lateral direction (as opposed to posterior, postero-lateral or anterior approaches). After the creation of the working channel, the intervertebral space is prepared as desired, including but not limited to the use of a device for decorticating the endplates to promote fusion. After disc space preparation, the spinal fusion implants 28 may then be introduced into the prepared intervertebral spaces.

As shown in FIG. 11, once the spinal fusion implants 28 are in place, the middle bone screw(s) 22 are secured to the targeted vertebral site. The middle bone screw(s) 22 are inserted into a patient through the surgical corridor such the middle bone screw(s) are attached into intermediate vertebral bodies. Once positioned as such, the cable 12 is either passed through apertures in the middle bone screw(s) 22 or loaded into the middle bone screw(s) 22. The step of securing middle bone screw(s) 22 to a vertebral body may be omitted depending on whether a single level or multi level system is being used. The use of middle bone screw(s) 22 is not necessary in a single level spinal alignment system.

FIG. 12 illustrates a second step involving the insertion of the superior bone screw 14. According to one embodiment of the present invention, the superior bone screw 14 is inserted into a patient through a surgical corridor such that the superior bone screw 14 is attached into the vertebral body immediately superior to the highest of the spinal fusion implants 28. Once positioned as such, the head member 30 of the cable 12 is loaded into the superior bone screw 14 and locked into position.

FIG. 13 illustrates a third step involving the insertion of the inferior bone screw 18. According to one embodiment of the present invention, the inferior bone screw 18 is inserted into a patient through a surgical corridor such that the inferior bone screw 18 is attached into the vertebral body immediately inferior to the lowest of the spinal fusion implants 28. Once positioned as such, the cable 12 may then be pulled or otherwise manipulated such that the distance between the superior bone screw 14, the inferior bone screw 18, and any middle bone screw(s) 22 is reduced. This serves to move the superior vertebral body, the inferior vertebral body, and any intermediate vertebral bodies so as to correct or minimize the spinal deformity. After this reduction, the main portion 32 of the cable 12 may be loaded and locked into inferior bone screw 18. Consequently, the inferior bone screw 18 maintains the superior vertebral body, inferior vertebral body, and any intermediate vertebral bodies in compression.

Figure 14:
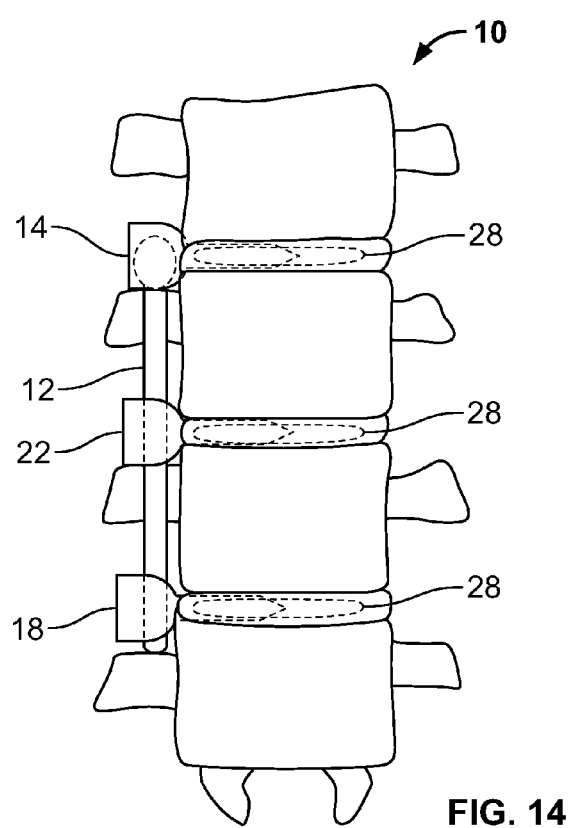
FIG. 14 is an anterior view illustrating a spinal alignment system according to an alternate embodiment of the present invention.
Figure 15:
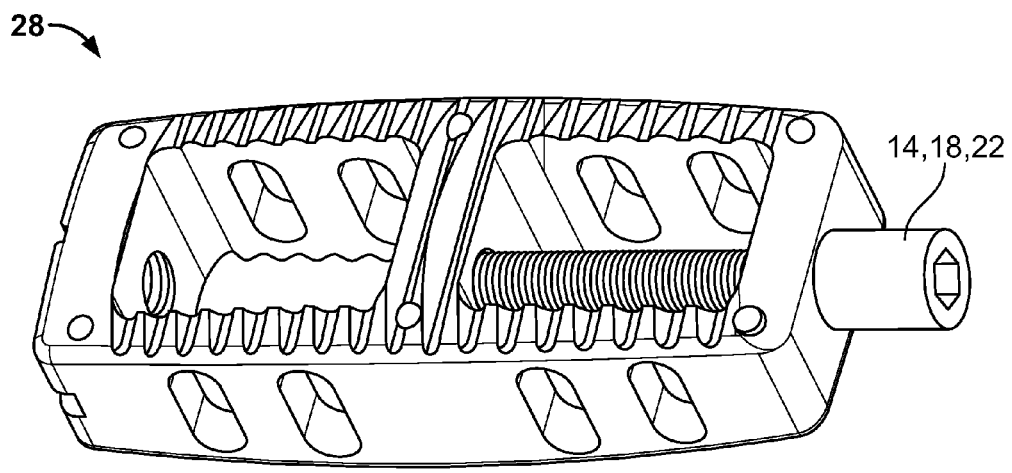
FIGS. 15-16 are perspective views of the spinal fusion implant of FIG. 14 with a bone screw extending partially through the implant (FIG. 15) and substantially through the entire implant (FIG. 16) according to the present invention.
Figure 16:
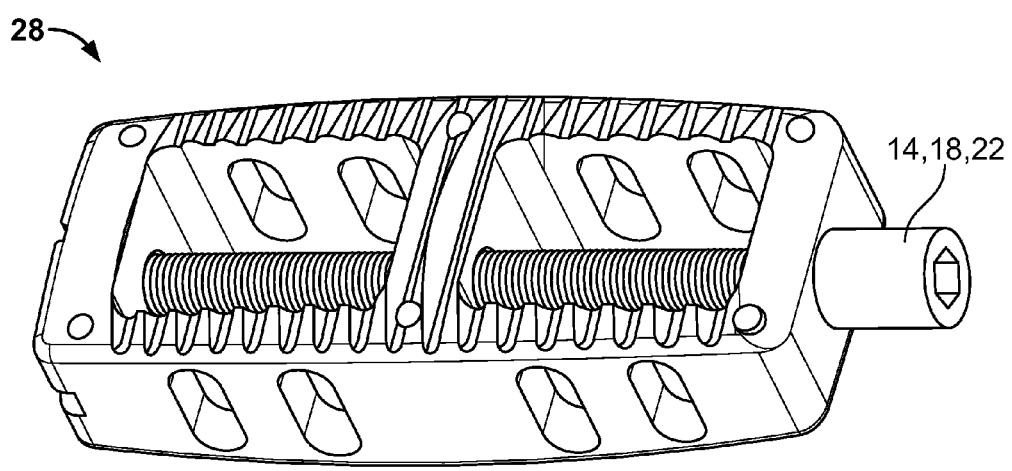

FIGS. 14-16 illustrates another exemplary embodiment of the present invention, wherein the spinal alignment system 10 is configured such that the superior bone screws 14, inferior bone screws 18, and/or middle bone screw(s) 22 may be secured directly into a spinal fusion implant 28 instead of being secured into the vertebral bodies. The bone screws (superior 14, inferior 18 or middle bone screw(s) 22) may be introduced into the implants 28 before, during and/or after the implants 28 are introduced into the respective intervertebral spaces. As shown in FIGS. 15-16, a bone screw (superior 14, inferior 18 or middle bone screw(s) 22) may be received into a spinal fusion implant 28 by either securing the bone screw substantially midway through the implant 28 (FIG. 15) or substantially through the entire implant 28 (FIG. 16). The cable 12 is coupled to the bone screws and is then capable of being pulled or otherwise manipulated to move the spinal implants 28 towards one another and thereby effect spinal deformity correction.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A system for treating spinal deformities comprising:
    an implant configured for introduction to an interbody space through a lateral approach having an upper surface including anti-migration elements to contact a first vertebra when said implant is positioned within the interbody space between the first vertebra and a second vertebra, a lower surface including anti-migration elements to contact said second vertebra when said implant is positioned within the interbody space, a distal wall, a proximal wall, a first sidewall to face an anterior aspect of said interbody space when said implant is positioned within the interbody space and a second sidewall to face a posterior aspect of said interbody space when said implant is positioned within the interbody space, said distal wall, proximal wall, first sidewall, and second sidewall comprising a radiolucent material, wherein said implant has a longitudinal length extending from a proximal end of said proximal wall to a distal end of said distal wall and a width extending from said first sidewall to said second sidewall, the implant having at least a first fusion aperture extending through said upper surface and lower surface and configured to permit bone growth between the first vertebra and the second vertebra when said implant is positioned within the interbody space, said first fusion aperture having: a longitudinal aperture length extending generally parallel to the longitudinal length of said implant, and a lateral aperture width extending between said first sidewall to said second sidewall, wherein the longitudinal aperture length is greater than the lateral aperture width; and
    a first bone screw configured for introduction through a lateral approach, the bone screw being securable to said first implant and including a tulip-shaped housing;
    a second bone screw dimensioned to be introduced through a generally lateral approach, the second bone screw being securable to one of the lateral aspect of a vertebral body and a second implant positioned in a second intervertebral space and including a tulip-shaped housing; and
    an elongate member configured to be coupled to said tulip-shaped housings of said first and second bone screws.

2. The system for treating spinal deformities of claim 1, further comprising:
    a third bone screw dimensioned to be introduced through a lateral approach and secured to at least one of the lateral aspects of a vertebral body, a second implant, and a third implant.

3. The system for treating spinal deformities of claim 1, wherein an angle between a screw portion and the tulip-shaped housing of at least one of said first and second bone screws is variable.

4. The system for treating spinal deformities of claim 1, wherein at least one of said first and second bone screws are cannulated.

5. The system for treating spinal deformities of claim 1, wherein the first end of said elongate member includes a shaped head member.

6. The system for treating spinal deformities of claim 1, wherein said elongate member is composed of at least one of steel, titanium, titanium alloy, nitinol, nylon, plastic, and polymer.

7. The system for treating spinal deformities of claim 1, wherein said elongate member is at least one of a cable and a rigid rod.

8. The system for treating spinal deformities of claim 1, further including a second fusion aperture extending through said upper surface and lower surface and configured to permit bone growth between the first vertebra and the second vertebra when said implant is positioned within the interbody space.

9. The system for treating spinal deformities of claim 8, further comprising a medial support extending between the first and second sidewalls and separating said first and second fusion apertures.

10. The spinal fusion implant of claim 1, wherein said implant includes at least one visualization aperture extending through at least one of said first sidewall and said second sidewall.

11. The system for treating spinal deformities of claim 1, wherein said elongate member is secured within the tulip-shaped housing of each of the first and second bone screws by a set screw.

12. A system for treating spinal deformities comprising:
    an implant configured for introduction to an interbody space through a lateral approach having an upper surface including anti-migration elements to contact a first vertebra when said implant is positioned within the interbody space between the first vertebra and a second vertebra, a lower surface including anti-migration elements to contact said second vertebra when said implant is positioned within the interbody space, a distal wall, a proximal wall, a first sidewall to face an anterior aspect of said interbody space when said implant is positioned within the interbody space and a second sidewall to face a posterior aspect of said interbody space when said implant is positioned within the interbody space, said distal wall, proximal wall, first sidewall, and second sidewall comprising a radiolucent material, wherein said implant has a longitudinal length extending from a proximal end of said proximal wall to a distal end of said distal wall and a width extending from said first sidewall to said second sidewall, the implant having at least a first fusion aperture extending through said upper surface and lower surface and configured to permit bone growth between the first vertebra and the second vertebra when said implant is positioned within the interbody space, said first fusion aperture having: a longitudinal aperture length extending generally parallel to the longitudinal length of said implant, and a lateral aperture width extending between said first sidewall to said second sidewall, wherein the longitudinal aperture length is greater than the lateral aperture width; and
    a first bone screw configured for introduction through a lateral approach and securable to said first implant;
    a second bone screw dimensioned to be introduced through a generally lateral approach and securable to one of the lateral aspect of a vertebral body and a second implant positioned in a second intervertebral space; and an elongate member configured to be coupled to said first and second bone screws, wherein a set screw is utilized to couple the elongate member to at least one of said first and second bone screws.

13. The system for treating spinal deformities of claim 12, wherein at least one of said first and second bone screws are variable angle screws.

14. The system for treating spinal deformities of claim 12, wherein at least one of said first and second bone screws are cannulated.

15. The system for treating spinal deformities of claim 12, wherein the first end of said elongate member includes a shaped head member.

16. The system for treating spinal deformities of claim 12, wherein said elongate member is composed of at least one of steel, titanium, titanium alloy, nitinol, nylon, plastic, and polymer.

17. The system for treating spinal deformities of claim 12, wherein said elongate member is at least one of a cable and a rigid rod.

18. The system for treating spinal deformities of claim 12, further including a second fusion aperture extending through said upper surface and lower surface and configured to permit bone growth between the first vertebra and the second vertebra when said implant is positioned within the interbody space.

19. The system for treating spinal deformities of claim 18, further comprising a medial support extending between the first and second sidewalls and separating said first and second fusion apertures.

20. The spinal fusion implant of claim 12, wherein said implant includes at least one visualization aperture extending through at least one of said first sidewall and said second sidewall.

21. The system for treating spinal deformities of claim 12, wherein said first and second bone screw each includes a tulip shaped housing.

22. The system for treating spinal deformities of claim 12, further comprising: a third bone screw dimensioned to be introduced through a lateral approach and secured to at least one of the lateral aspects of a vertebral body, a second implant and a third implant.

23. A system for treating spinal deformities comprising:
an implant configured for introduction to an interbody space through a lateral approach having an upper surface including anti-migration elements to contact a first vertebra when said implant is positioned within the interbody space between the first vertebra and a second vertebra, a lower surface including anti-migration elements to contact said second vertebra when said implant is positioned within the interbody space, a distal wall, a proximal wall, a first sidewall to face an anterior aspect of said interbody space when said implant is positioned within the interbody space and a second sidewall to face a posterior aspect of said interbody space when said implant is positioned within the interbody space, said distal wall, proximal wall, first sidewall, and second sidewall comprising a radiolucent material, wherein said implant has a longitudinal length extending from a proximal end of said proximal wall to a distal end of said distal wall and a width extending from said first sidewall to said second sidewall, the implant having at least a first fusion aperture extending through said upper surface and lower surface and configured to permit bone growth between the first vertebra and the second vertebra when said implant is positioned within the interbody space, said first fusion aperture having: a longitudinal aperture length extending generally parallel to the longitudinal length of said implant, and a lateral aperture width extending between said first sidewall to said second sidewall, wherein the longitudinal aperture length is greater than the lateral aperture width; and
a first bone screw configured for introduction through a lateral approach and securable to said first implant;
a second bone screw dimensioned to be introduced through a generally lateral approach and secured to one of the lateral aspect of a vertebral body and a second implant positioned in a second intervertebral space;
an elongate member configured to be coupled to said first and second bone screws; and
a third bone screw dimensioned to be introduced through a lateral approach and securable to at least one of the lateral aspect of a vertebral body, a second implant, and a third implant, the third bone screw including a side-loading housing dimensioned to receive said elongate member therethrough.

* * * * *